US008906702B2

(12) United States Patent
Zahn et al.

(10) Patent No.: US 8,906,702 B2
(45) Date of Patent: Dec. 9, 2014

(54) METHODS AND RELATED DEVICES FOR CONTINUOUS SENSING UTILIZING MAGNETIC BEADS

(75) Inventors: Jeffrey Zahn, Princeton, NJ (US); Lawrence Anthony Sasso, Jr., New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 533 days.

(21) Appl. No.: 13/123,547

(22) PCT Filed: Mar. 31, 2009

(86) PCT No.: PCT/US2009/038880
§ 371 (c)(1), (2), (4) Date: May 2, 2011

(87) PCT Pub. No.: WO2010/042242
PCT Pub. Date: Apr. 15, 2010

(65) Prior Publication Data
US 2011/0201125 A1 Aug. 18, 2011

Related U.S. Application Data

(60) Provisional application No. 61/104,468, filed on Oct. 10, 2008.

(51) Int. Cl.
*G01N 33/533* (2006.01)
*B01L 3/00* (2006.01)

(52) U.S. Cl.
CPC ..... *B01L 3/502776* (2013.01); *B01L 2400/043* (2013.01); *B01L 3/502707* (2013.01); *B01L 2300/0816* (2013.01); *B01L 2200/0636* (2013.01); *B01L 3/502761* (2013.01); *B01L 2400/0478* (2013.01)
USPC .......................................... 436/526; 422/408

(58) Field of Classification Search
CPC .................... B01L 3/502761; B01L 2400/043; B01L 2200/0668; B01L 2300/0816; B01L 2300/0867; B01L 3/50273; C12Q 2565/629; C12Q 1/6834; C12Q 2563/143; C12Q 2563/149; C12Q 2563/107; G01N 33/54326; G01N 33/54366; G01N 33/54313; G01N 33/53; G01N 33/582; G01N 35/0098; G01N 27/44791; G01N 27/745; G01N 2015/149
USPC .......................................................... 422/408
See application file for complete search history.

(56) References Cited

U.S. PATENT DOCUMENTS 6,541,213 B1 4/2003 Weigl et al.
(Continued)

FOREIGN PATENT DOCUMENTS

WO 2011/049718 4/2011

OTHER PUBLICATIONS

Sasso and Zahn, "Continuous Microfluidic Immunosensing with Antibody Conjugated Paramagnetic Beads", 12th International Conference on Miniaturized Systems for Chemistry and Life Sciences, Oct. 2008, CA, USA.*
(Continued)

*Primary Examiner* — Yelena G Gakh
(74) *Attorney, Agent, or Firm* — Fox Rothschild LLP

(57) ABSTRACT

A fluidic device including a main channel, wherein a first inlet fluidly connects to an upstream end of the main channel and introduces magnetic beads into a first side of the main channel A second inlet is fluidly connected to the upstream end of the main channel and introduces a sample stream into a second side of the main channel A first magnet disposed adjacent to the second side of the main channel pulls the magnetic beads towards a sidewall of the second side, and thus into the sample stream A second magnet disposed downstream from the first magnet and adjacent to a first side of the main channel subsequently pulls the magnetic beads towards a sidewall of the first side, and thus out of the sample stream A detection region is disposed at or downstream from the second magnet and in the first side of the main channel.

10 Claims, 16 Drawing Sheets

(56) References Cited

U.S. PATENT DOCUMENTS

| | | | | |
|---|---|---|---|---|
| 2003/0211507 | A1 | 11/2003 | Hatch et al. | |
| 2008/0124779 | A1* | 5/2008 | Oh et al. | 435/173.9 |
| 2011/0201125 | A1 | 8/2011 | Zahn et al. | |

OTHER PUBLICATIONS

Sasso et al., "Autonomous magnetically actuated continuous flow microimmunofluorocytometry assay", Microfluid Nanofluidics, 2010, v. 9, No. 2-3, pp. 253-265.*

Suzuki et al. "A Chaotic Mixer for Magnetic Bead-Based Micro Cell Sorter", J. Microelectrochem. Systems, 2004. v. 13, No. 5, pp. 779-790.*

Choi, et al. "A New Magnetic Bead-Based, Filterless Bio-Separator with Planar Electromagnet Surfaces for Integrated Bio-Detection Systems." Sensors and Actuators B (2000), 68(1-3): 34-39.

Choi, et al. "An Integrated Microfluidic Biochemical Detection System for Protein Anaylsis with Magnetic Bead-Based Sampling Capabilities." Lab on a Chip (2002), 2(1): 37-30.

Kim, et al. "Magnetic Force-Based Multiplexed Immunoassay Using Superparamagnetic Nanoparticles in Microfluidic Channel." Lab on a Chip (2005), 5(6): 657-664.

Fan, et al. "Dynamic DNA Hybridization on a Chip Using Paramagnetic Beads." Analytical Chemistry (1999), 71(21): 4851-4859.

Hayes, et al. "Flow-Based Microimmunoassay." Analytical Chemistry (2001), 73(24): 5896-5902.

Sasso et al., "Microfluidic Processing Platform for Multiplexed Magnetic Bead Immunoassys", 15th International Conference on Miniaturized Systems for Chemistry and Life Sciences, Oct. 2-6, 2011, Seattle, WA, retrieved from: http://www.rsc.org/images/LOC/2011/PDFs/Papers/068_0116.pdf.

International Search Report and Written Opinion issued Aug. 1, 2013, in Application No. PCT/2013/036768.

* cited by examiner

200

METHODS AND RELATED DEVICES FOR CONTINUOUS SENSING UTILIZING MAGNETIC BEADS

CROSS-REFERENCE TO RELATED APPLICATIONS

This application is the U.S. National Phase of International Patent Application Serial No. PCT/US09/38880, filed Mar. 31, 2009, which claims the benefit of U.S. Provisional Patent Application Ser. No. 61/104,468, filed on Oct. 10, 2008, both of which are incorporated herein by reference in their entireties.

STATEMENT REGARDING FEDERALLY SPONSORED RESEARCH

This invention was made with government support under Grant No. 1R21HL084367-01A1 awarded by the National Institutes of Health. The government has certain rights in the invention.

FIELD OF THE INVENTION

Various aspects of the invention relate generally to detection methods and devices that employ microfluidics. More particularly, various embodiments disclose devices and related methods that employ paramagnetic beads and magnets disposed along a fluidic channel to detect an analyte.

BACKGROUND OF THE INVENTION

Traditional methods for measuring concentrations of an analyte in a sample, and in particular protein analytes, rely on bench top procedures with sequential steps. These assays, such as Enzyme-Lined ImmunoSorbent Assay (ELISA), and assays utilizing flow cytometry, require relatively large sample volumes and typically require many hours to complete. Further, these assays do not lend themselves to inexpensive automation.

Accordingly, there is an immediate need for improved assays that employ relatively small sample sizes, complete relatively quickly and which are easy to deploy.

SUMMARY OF THE INVENTION

One aspect of the invention discloses a fluidic device that may be used to detect an analyte in a sample stream. The fluidic device includes a main channel that is sized to accept magnetic beads and permits fluidic flow of the magnetic beads along the main channel. The main channel has an upstream end, a downstream end, a first side, and a second side. The first side and second side may include respective sidewalls of the fluidic channel. A first inlet fluidly connects to the upstream end of the main channel and introduces the magnetic beads into the main channel. A second inlet is fluidly connected to the upstream end of the main channel and introduces the sample stream into the second side of the main channel. A first magnet disposed adjacent to the second side of the main channel pulls the magnetic beads towards the sidewall of the second side, and thus into the sample stream. A second magnet disposed downstream from the first magnet and adjacent to the first side of the main channel subsequently pulls the magnetic beads towards the sidewall of the first side, and thus out of the sample stream. A detection region is disposed in the downstream end of the main channel and in the first side of the main channel. In various embodiments the detection region is disposed at or downstream from the second magnet.

In some embodiments the magnetic beads are introduced into a central portion of the main channel. In these embodiments the fluidic device further includes a third inlet that provides a wash stream that flows past the second magnet on the first side of the main channel.

In other embodiments the first inlet is configured to introduce the magnetic beads into the first side of the main channel. In certain preferred embodiments the main channel includes a wall at or upstream to the first magnet that separates the magnetic beads from the sample stream. In particularly preferred embodiments the wall begins upstream to the first magnet and terminates at or upstream to the first magnet.

In certain preferred embodiments the detection region comprises a divot in the sidewall of the first side of the main channel.

Other embodiments provide for devices with multiple stages, in which each stage performs one or more processing function. Such embodiments include a third magnet and a fourth magnet. The third magnet is disposed adjacent to the first side of the main channel downstream from the first magnet and positioned to pull the magnetic beads towards the sidewall of the first side. The fourth magnet is disposed adjacent to the second side of the main channel downstream from the third magnet and upstream to the second magnet and positioned to pull the magnetic beads towards the sidewall of the second side. A first wash inlet provides a first wash stream to the first side of the main channel at or upstream to the third magnet. A tag inlet provides a tag stream to the second side of the main channel at or upstream to the fourth magnet. Finally, a second wash inlet provides a second wash stream to the first side of the main channel at or upstream to the second magnet.

In preferred embodiments of a multi-stage device, the device further includes a first outlet fluidly coupled to the main channel at or downstream from the third magnet that runs to waste one or more streams flowing along the second side of the main channel, and a second outlet fluidly coupled to the main channel at or downstream from the second magnet that runs to waste one or more streams flowing along the second side of the main channel.

Another aspect of the invention discloses an assay method. The assay method employs a fluidic channel having first and second sides. Magnetic beads are introduced into the fluidic channel, in which the magnetic beads are configured to interact with an analyte for detection of the analyte. A sample stream comprising the analyte is introduced into the second side of the fluidic channel. The magnetic beads are then magnetically induced to enter into the sample stream and travel along in the sample stream, thus performing an incubation step. Then, the magnetic beads are magnetically induced to enter into a second stream flowing along the first side of the fluidic channel. In various embodiments the second stream is a wash stream. A detection step is then performed for the magnetic beads passing through a detection region located on the first side of the fluidic channel. In various embodiments the detection step comprises an optical detection step.

In some embodiments the magnetic beads are introduced into the first side of the fluidic channel. In other embodiments the magnetic beads are introduced into a central portion of the fluidic channel.

DETAILED DESCRIPTION

Figure 1:
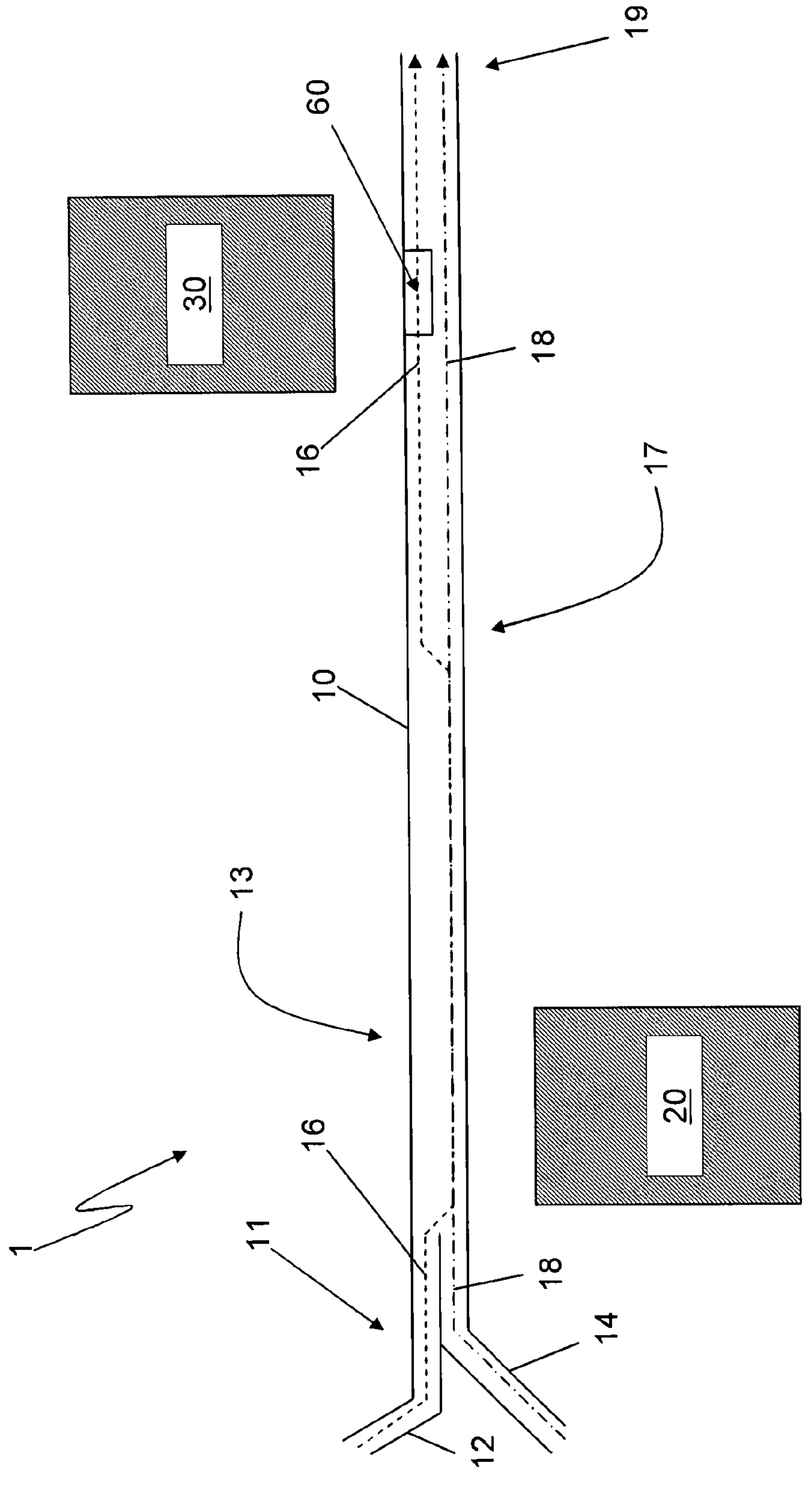
FIG. 1 illustrates an embodiment sensing device.

FIG. 1 is a top plan view illustrating one aspect broadly employed by various embodiments. A detection device 1 includes a fluidic channel 10, a first magnet 20 and a second magnet 30. The channel 10 has an upstream end 11 and a downstream end 19 as defined by fluid flowing within the channel 12. The channel 10 is a microfluidic channel, and may be, for example, about 300 μm wide and 20 μm deep, although other dimensions are certainly possible. Dimensions of the channel 10 may depend, for example, upon the strength of the magnets 20, 30 used, in which wider channels 10 may require stronger magnets 20, 30. The depth of the channel 10 may be determined by, for example, the depth of field of the detection equipment and the size of the magnetic beads used. Typically, the maximum width of the channel 10 is less than 1 mm. The channel 10 also includes a first side 13 and a second side 17, which respectively run along the length of the channel 10 and are preferably defined in part by opposite sidewalls of the channel 10. Any suitable technique may be used to manufacture the device 1.

The upstream end 11 of the channel 10 includes a first inlet 12 and a second inlet 14. The first inlet 12 is preferably disposed on the first side 13 of the channel 10; that is, fluids fed into the channel 10 by the inlet 12 are fed into the first side 13 of the channel 10, and therefore flow along a sidewall on the first side 13 of the channel. The second inlet 14 is preferably disposed on the side opposite that of the first inlet 12, and hence is disposed on the second side 17 of the fluidic channel 10; that is, the second inlet 14 is positioned so that fluids provided into the main channel 10 by the second inlet 14 flow along the sidewall of the second side 17. Because of the scale of the fluidic channel 10, the flow of fluids respectively introduced into the channel 10 by the inlets 12, 14 is laminar; very little mixing occurs between these laminar flows.

The second inlet 14 is used to introduce into the channel a sample fluid containing a target analyte that is to be assayed. The first inlet 12 is used to introduce into the channel 10 a stream of paramagnetic beads. These beads have a surface that has been configured to bind to, or otherwise detectably interact with, the target analyte. These beads are preferably suspended in a carrier medium that has a density that is close to that of the beads, and it is this suspension of beads with the carrier medium that is introduced in the channel 10 via first inlet 12. The beads may be of any size, shape and material construction so as to provide suitable characteristics for the detection methods as discussed in more detail below. By way of example, the beads may be about 8 μm in diameter and made from polystyrene impregnated with 2.4% magnetite by weight. For such beads, Ficoll-Paque PLUS from GE Healthcare may be employed as the carrier medium.

As the beads move into the channel 10 from the first inlet 12 they are pulled against the sidewall of the second side 17 of the channel 10 by the first magnet 20. The first magnet 20 is positioned adjacent to the second side 17 of the main channel 10 so that the first magnet 10 pulls the beads towards the sidewall of the second side 17 of the channel 10. It will be appreciated that the term “adjacent” is intended to include configurations in which there is a gap between the magnet and the corresponding sidewall towards which it is positioned to pull the beads. The exact positioning of the first magnet 20 with respect to the channel 10 is a design choice based upon the types of materials used, as well as the size and length of the channel 10, and may be determined quite easily experimentally. The first magnet 20 pulls the beads into the laminar flow of the sample fluid introduced into the channel 10 by second inlet 14. The trajectory of the beads is indicated by dashed line 16, whereas the trajectory of the sample fluid is indicated by dot-dashed line 18. The beads 16 travel along the second side 17 of the channel 10 for a period of time determined by the flow rate in the channel 10; hence, the effective incubation time of the beads 16 with the sample fluid 18 may be controlled by the length of the channel 10 and the flow rate of fluid within the channel 10.

At a position predetermined by the placement of the second magnet 30 on the first side 13 along the channel 10, the beads 16, pulled by the second magnet 30, transition from moving along the second side 17 of the channel 10 to moving along the first side 13 of the channel 10. The beads 16 thus exit out of the laminar flow 18 of the sample fluid and into the laminar flow of the carrier medium. The beads then pass through a detection region 60 at which they are scanned to determine if they have interacted with any of the target analyte. The detection region 60 is preferably as close to the first side 13 of the channel 10 as possible to avoid the possibility of cross-contamination with the sample fluid 18 passing by on the opposite side 17 of the channel 10. The detection region 60 is thus preferably entirely contained within the flow path of the carrier fluid passing along the first side 13 of the channel 10. It will be appreciated that by controlling the length of the channel 10 and the flow rate of the fluids 16, 18 within the channel 10 that incubation of the beads with the target analyte can be controlled to keep the detection properties of the beads in a linear range for subsequent detection in region 60.

Any suitable equipment may be used to perform assay detection in the detection region 60. Simply by way of example, a suitably tuned laser in conjunction with an appropriate photomultiplier tube (PMT) may be used together to detect beads that have interacted with the target analyte. Such beads may appear as a spike or the like in intensity levels, which may be detected (such as by amplitude), filtered, and averaged by any suitable means to obtain an average reading over a predetermined period of time, which may be from, for example, seconds to minutes. Other types of detection equipment may be based upon, for example, changes in electrical impedance as the beads pass through the detection region 60.

The above assay, and the related method which it employs, represents a single stage device. A benefit of this is that devices employing multiple stages may be employed, with each stage performing a respective task or tasks, such as incubation, washing, and detection. One or more outlets may be set in or between the stages to draw off fluids introduced upstream, while one or more inlets also set in or between the stages may provide fluids for processing downstream. For example, in one embodiment, a device 100, shown conceptually in FIG. 2, uses a two-stage magnetically actuated binding scheme. In the first stage 101, paramagnetic beads coated with monoclonal antibodies are incubated with the antigen of interest, i.e., the target analyte. The beads are then transferred into the second stage 102 of the device 100 where they are incubated with a fluorescently tagged antibody. The concentration of the target analyte antigen is measured based upon the fluorescence intensity of the incubated beads. The entire assay is completed on-chip. The device 100 may be used, for example, to measure the concentration of fluorescently tagged biotin (biotin-FITC), although it will be appreciated that the device, in conjunction with suitably configured beads, may be used to measure other types of analytes. Various device and their related benefits and methods are discussed in more detail in the following.

Single Stage Device

Figure 3:
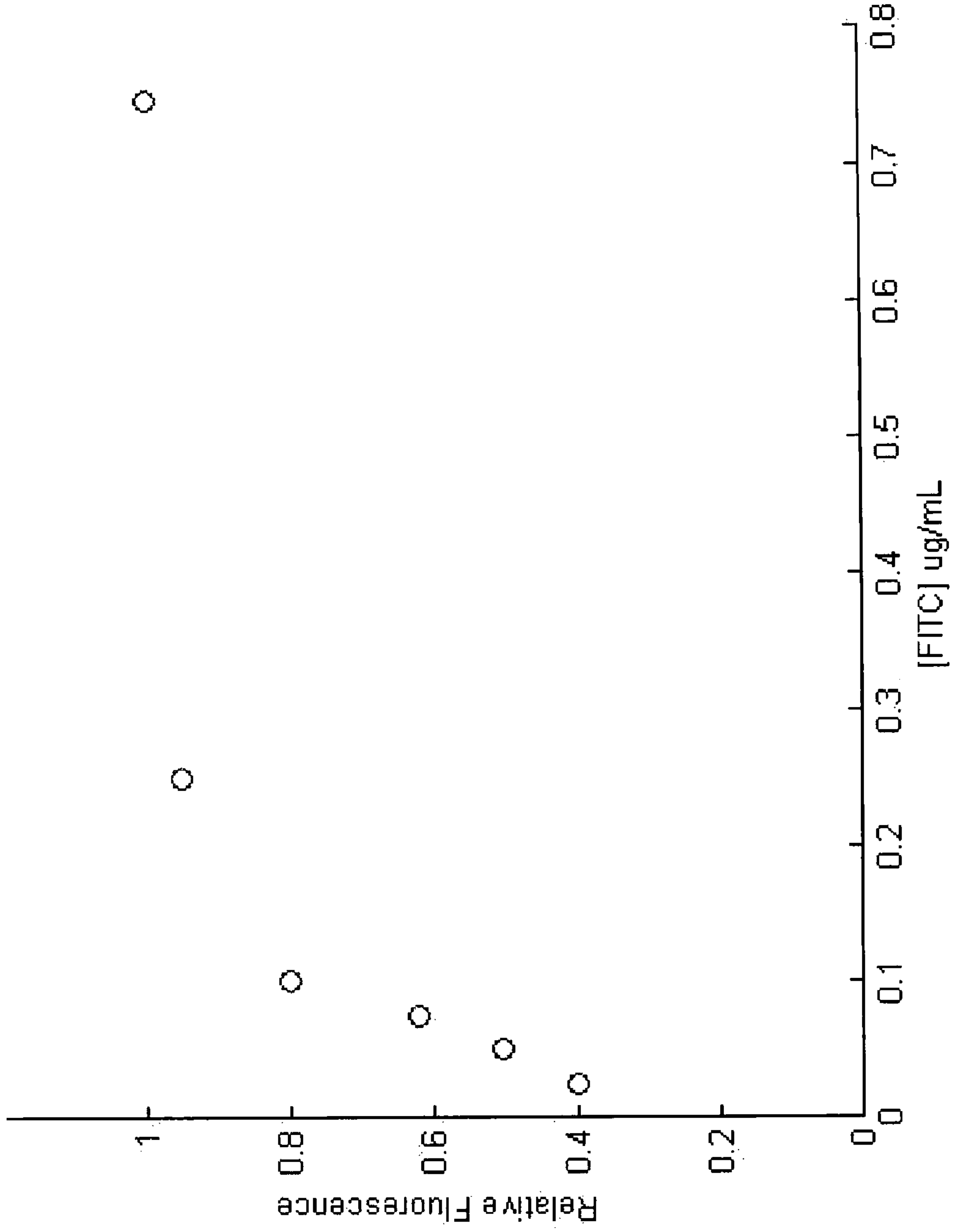
FIG. 3 is a graph of mean peak intensity versus concentration for a 30 second bench incubation, showing saturation above 300 ng/ml.

By way of a specific example, a complete microfluidic immunoassay has been fabricated and tested which measures the concentration of a specific protein in a sample stream. A single-stage device 200, shown in FIGS. 4 and 5, was tested that used streptavidin coated paramagnetic beads (Bangs Laboratories, Inc., Fisher, Ind.) to continuously measure the concentration of a biotin-FITC sample stream 218. To determine the optimal conditions for the streptavidin-biotin binding, a bench-top incubation test was performed. The beads were incubated with the biotin-FITC solution at varying concentrations in an eppendorf tube for 30 seconds. The beads were then washed with PBS and re-suspended in a buffer. The bead fluorescence was then determined using an argon ion laser and PMT detection, discussed below, with a microfluidic focusing device. This test demonstrated fluorescence saturation due to complete biotin binding on the bead surface for concentrations greater than 300 ng/ml, as indicated by FIG. 3.

Figure 4B:
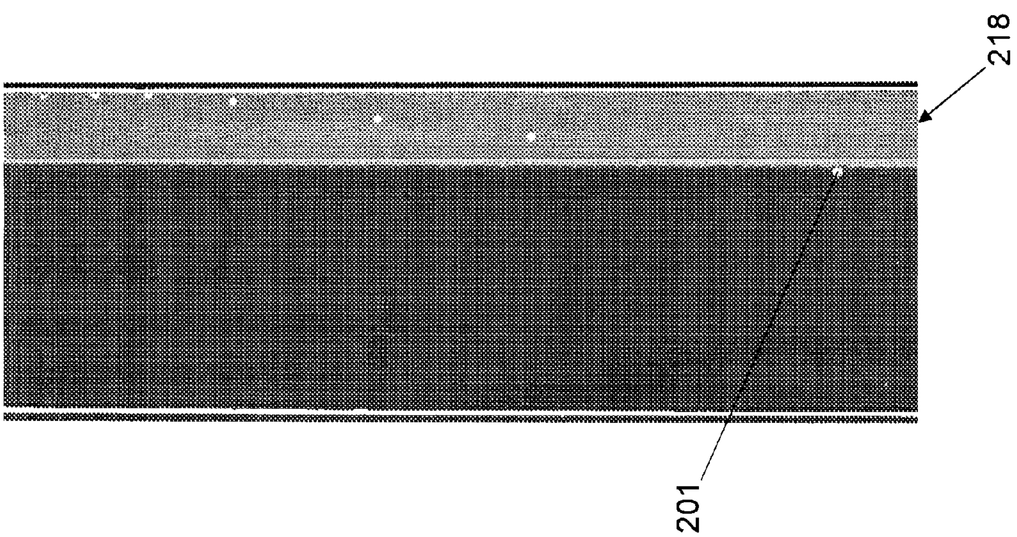
FIG. 4B is a composite micrograph of beads entering a sample stream.
Figure 4A:
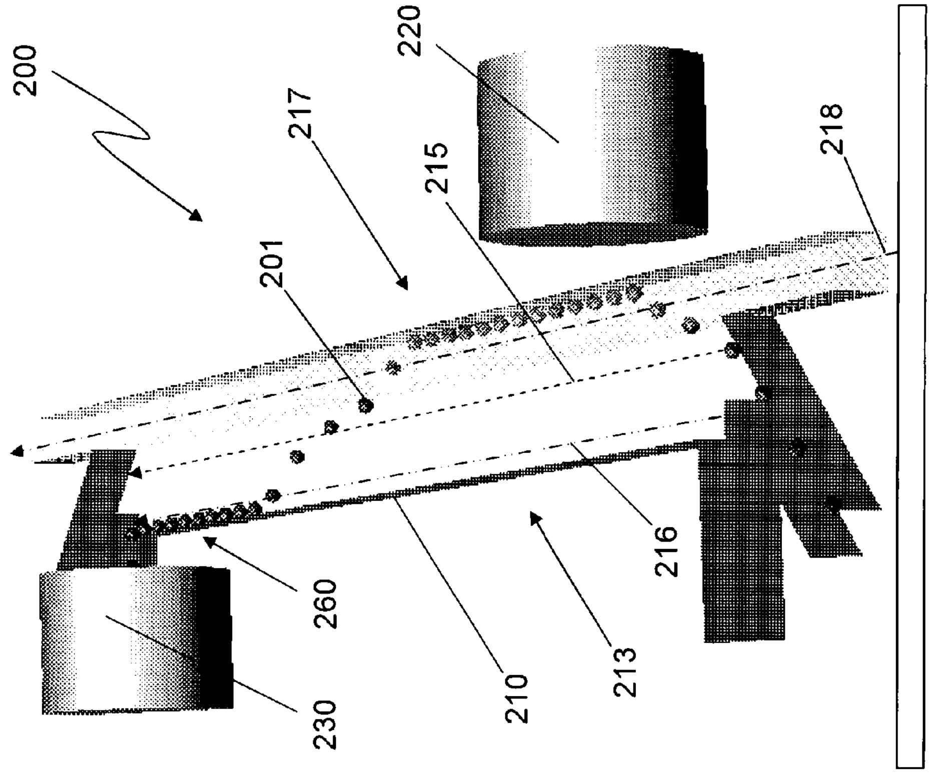
FIG. 4A illustrates a single-stage embodiment microfluidic device.
Figure 5:
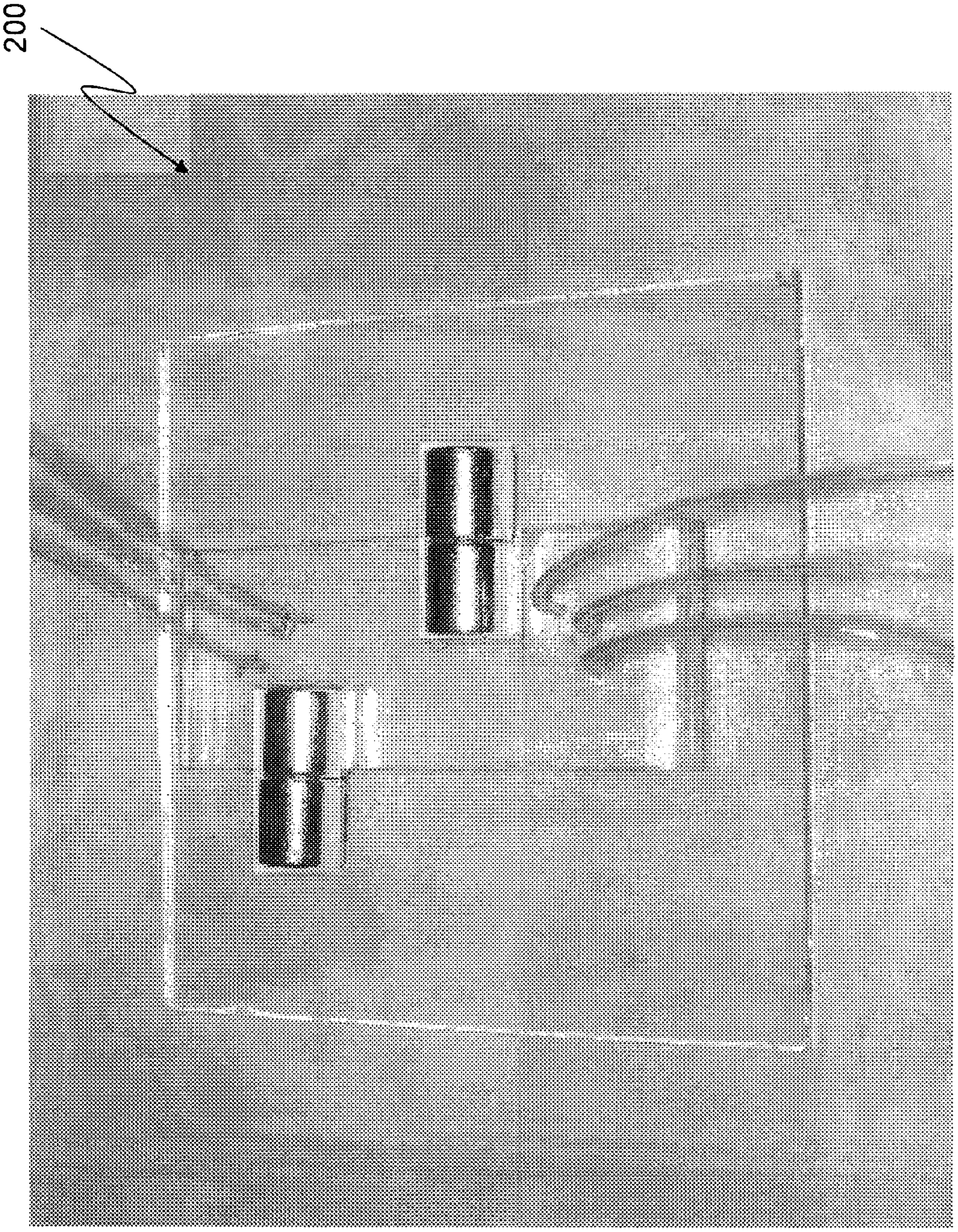
FIG. 5 is a photograph of the device indicated in FIG. 4.

The incubation was then replicated in the microfluidic device 200. The microdevice 200 includes a 300 μm wide, 20 μm deep channel 210 with three inlets and three outlets for respective stream 215, 216, 218, as well as actuating magnets 220, 230. The streptavidin-coated paramagnetic beads 201 are introduced into a central portion of the main channel 210 in a carrier fluid stream 215. The adjacent channels carry the biotin-FITC stream 218 and a wash stream 216. Magnets 220, 230 on opposite respective sides 217, 213 of the channel 210 manipulate the beads 201 as they flow down the channel 210. FIG. 4A illustrates the microdevice 200, and FIG. 4B is a composite micrograph of beads 201 entering the biotin-FITC stream 218, which is the grey area in the right of FIG. 4B.

As each bead 201 enters the main channel 210, it is immediately pulled into the biotin-FITC sample stream 218 by the first magnet 220. There is minimal mixing between the three streams 215, 216, 218 since the flow is laminar at this scale. The Reynolds number for this channel 210 with the flow rates used is approximately $5\times10^{-8}$. The beads 201 are pulled to the sidewall on the second side 217 of the channel 210, and remain against the sidewall of the second side 217 as they travel down the length of the channel 210. As discussed earlier, 8 μm diameter polystyrene beads impregnated with 2.4% magnetite by weight were used. This gives the beads 201 sufficient paramagnetic composition to be pulled strongly by neodymium magnets 220, 230, which may have a surface field of 4,680 Gauss. As the beads 201 roll along the sidewall of the second side 217 of the device 200, streptavidin-biotin binding occurs. At a prescribed location downstream, the beads 201 are pulled across the channel 210 by the second magnet 230 into the wash stream 216 on the first side 213 of the channel 210. Again, the beads 201 roll along the sidewall of the first side 213 of the channel 210.

At the end of the device 200 is the detection region 260. An argon ion laser with a 488 nm emission is focused on the first side 213 of the channel 210 where the beads 201 pass, carried by the wash fluid 216. The PMT measures the fluorescence intensity of each bead 201 as it passes over the laser beam in the detection region 260. The mean fluorescence intensity over a period of time is representative of the biotin-FITC concentration in the sample 218. This period of time is the sample interval of the system 200, and can be in the range of a few seconds to a few minutes depending on the concentration of beads 201 as well as the desired signal-to-noise ratio. Lower sample rates may result in more precise measurements which are more noise-immune.

Due to edge effects, the beads 201 traverse the channel 210 significantly more slowly at the edges than they would farther from the sidewalls. This phenomenon is beneficial to the design of the microdevice 200 since it allows long bead 201 residence times even with relatively high flow rates. For the flow rates used in experiments with this device, the calculated average fluid velocity in the main channel 210 is 2.5 mm/sec. Thus, the theoretical range of velocities across the channel is from 3.75 mm/sec at the center to near zero at the edges. Ignoring other forces, the bead 210 velocity should be equal to the fluid velocity at the centroid of the bead 201. The velocity at a point 4 μm from the sidewall for the parabolic flow profile described in a 300 μm wide channel is 0.93 mm/sec. The bead 201 velocity was found empirically to be approximately 0.55 mm/sec. The actual velocity is expected to be lower than that found through fluid velocity alone due to friction between the bead 201 and the sidewalls of the first side 213 and second side 217 of the channel 210.

Samples were run on the device 200 as described above on an epifluorescent microscopy platform. By tailoring the fluid flow rates to 0.3 μl/min, the beads 201 had a residence time in the biotin-FITC solution 218 of 18 seconds. The flow rate and thus the residence time may be chosen such that the range of sample concentrations to be measured falls in the linear part of the curve. If the time is too long, the higher concentration samples may saturate, thus having identical readings. If the time is too short, the signal-to-noise ratio may be poor and measurements may thus be imprecise.

Data from the PMT may be processed by a filtering and peak-finding algorithm. The data may first be high-pass filtered with, for example, a first order Butterworth filter with a cutoff frequency of 1 Hz. Next, the data set may be parsed with a peak-finding algorithm that records all amplitude drops greater than a threshold value. The threshold may be set, for example, at two times the standard deviation of the data set. This threshold algorithm has given results that correlate well with those obtained from flow cytometry.

Figure 6:
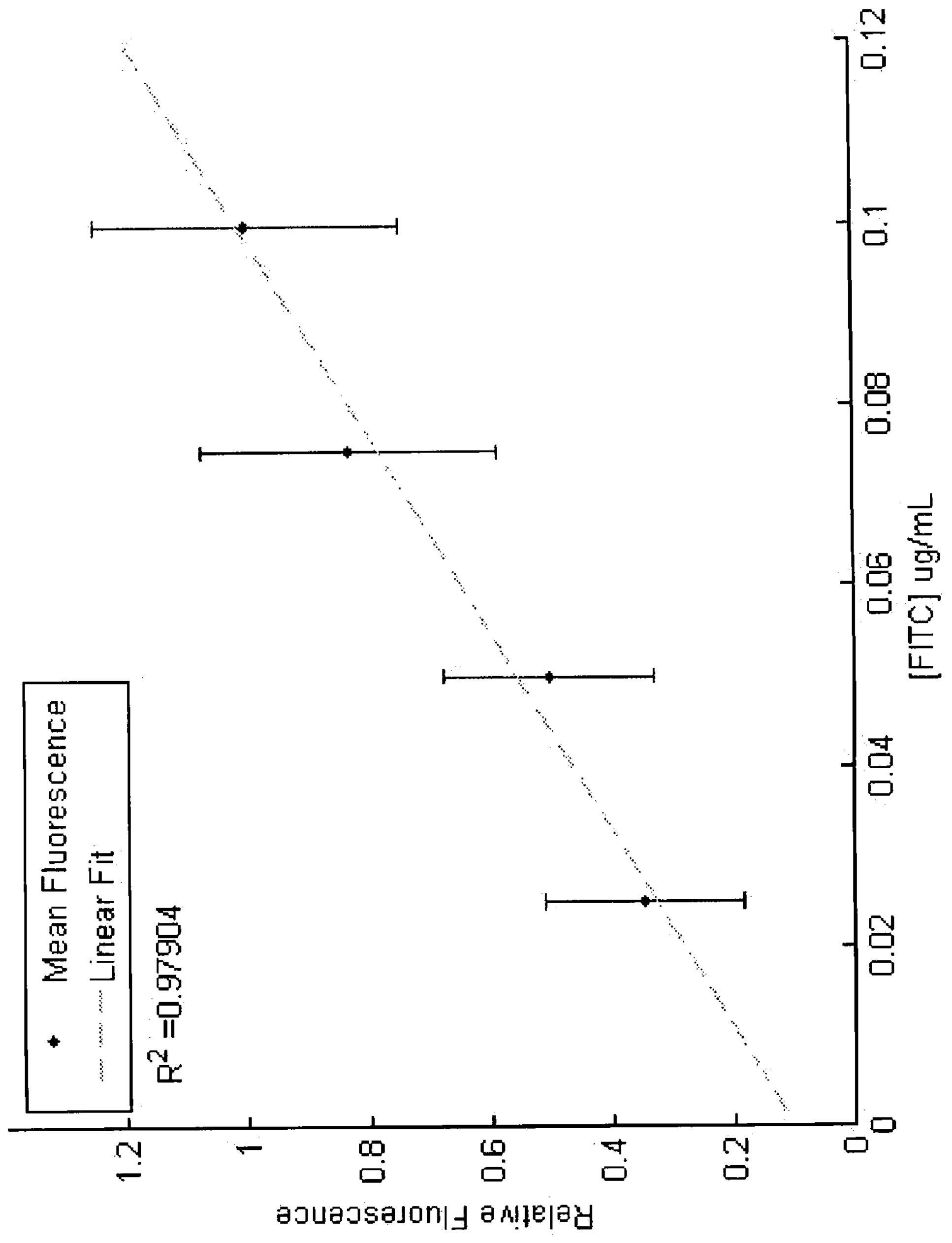
FIG. 6 is a graph of relative fluorescence versus target analyte concentration for the microdevice indicated in FIGS. 4 and 5, with standard deviation (error bars).

Data from the microdevice assay 200 have shown that the device 200 is capable of accurately measuring the concentration of biotin-FITC in a sample stream 218. The data show good linearity, which lends itself to the development of a calibration curve. Thus, the device 200 could be used for both relative and absolute measurement of sample 218 concentrations. FIG. 6 show the results from one run of the assay 200. The sample periods were 30 seconds for all samples.

The error bars in FIG. 6 show the standard deviations of individual bead 201 intensities over the sample period. The large range of bead 201 intensities suggests that for sample periods significantly shorter than 30 seconds the measurement precision may be poor. Longer sample periods would be expected to increase the precision.

Figure 7:
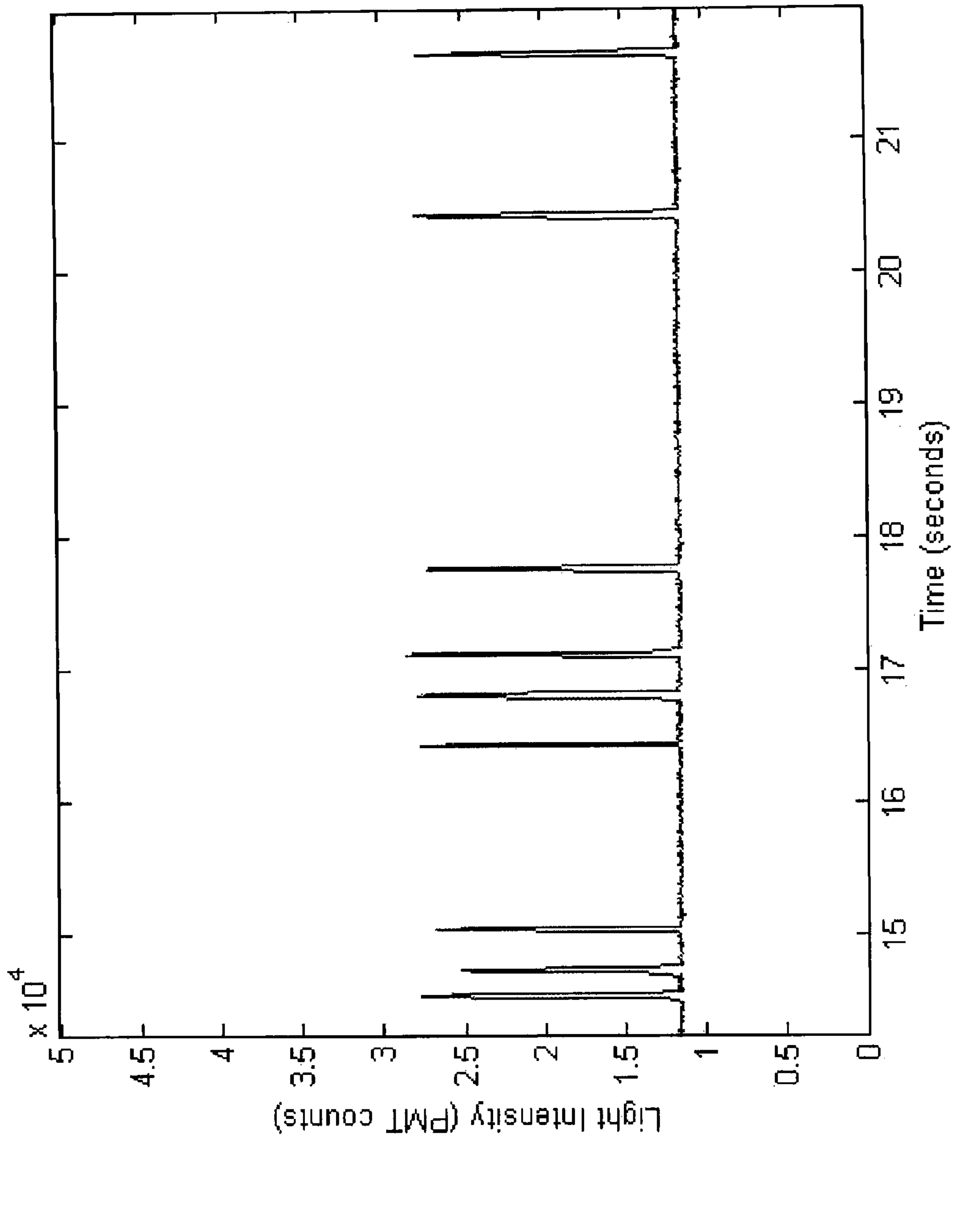
FIG. 7 is a graph of sample photomultiplier tube output for the microdevice assay indicated in FIGS. 4 and 5, using a 30× objective.

FIG. 7 displays a sample PMT output before high-pass filtering. Each peak represents a passing bead 201. Filtering shifts the baseline to zero and shifts all of the peaks down by an equal amount. Any drift in the signal, which can be caused by flow anomalies or variations in ambient light, is removed by the filter. Subsequently, the data set has only the peaks due to fluorescent beads 201, and small amplitude, high frequency noise. For the data in FIG. 6, the noise amplitude was significantly below the peak threshold for all four samples. As peak intensities decrease due to lower sample concentrations, the threshold approaches the noise floor, and precision may therefore suffer. Thus, if the desired measurement range yields low fluorescence intensities, the flow rate may be decreased to achieve a longer incubation time. Very low flow rates, such as below 100 nl/min, may introduce implementation problems related to long flow settling times and beads 201 sticking in the channel 210 due to low shear.

The device 200 may be fabricated using soft lithography of polydimethylsiloxane (PDMS). The inlet and outlet ports of the device 200 may be punched, for example, with a 19 gauge needle. The PDMS chip may then be bonded to a glass slide. Finally, Tygon tubing (0.1 inch ID) or the like may be pressed into the ports of the chip and retained by friction. A syringe pump or the like infuses the three inlet fluids from, for example, 1 cc plastic syringes.

The magnet 220, 230 positioning is of relatively low impact to the proper functioning of the microdevice 200. Optimal placement was initially found by trial and error, and a template was created. From the template, new devices 200 can easily be made which function properly without further tuning. The magnets 220, 230 may be held in place by friction within notches in the PDMS, which can be cut with a razor blade.

Two Stage Device

Figure 2:
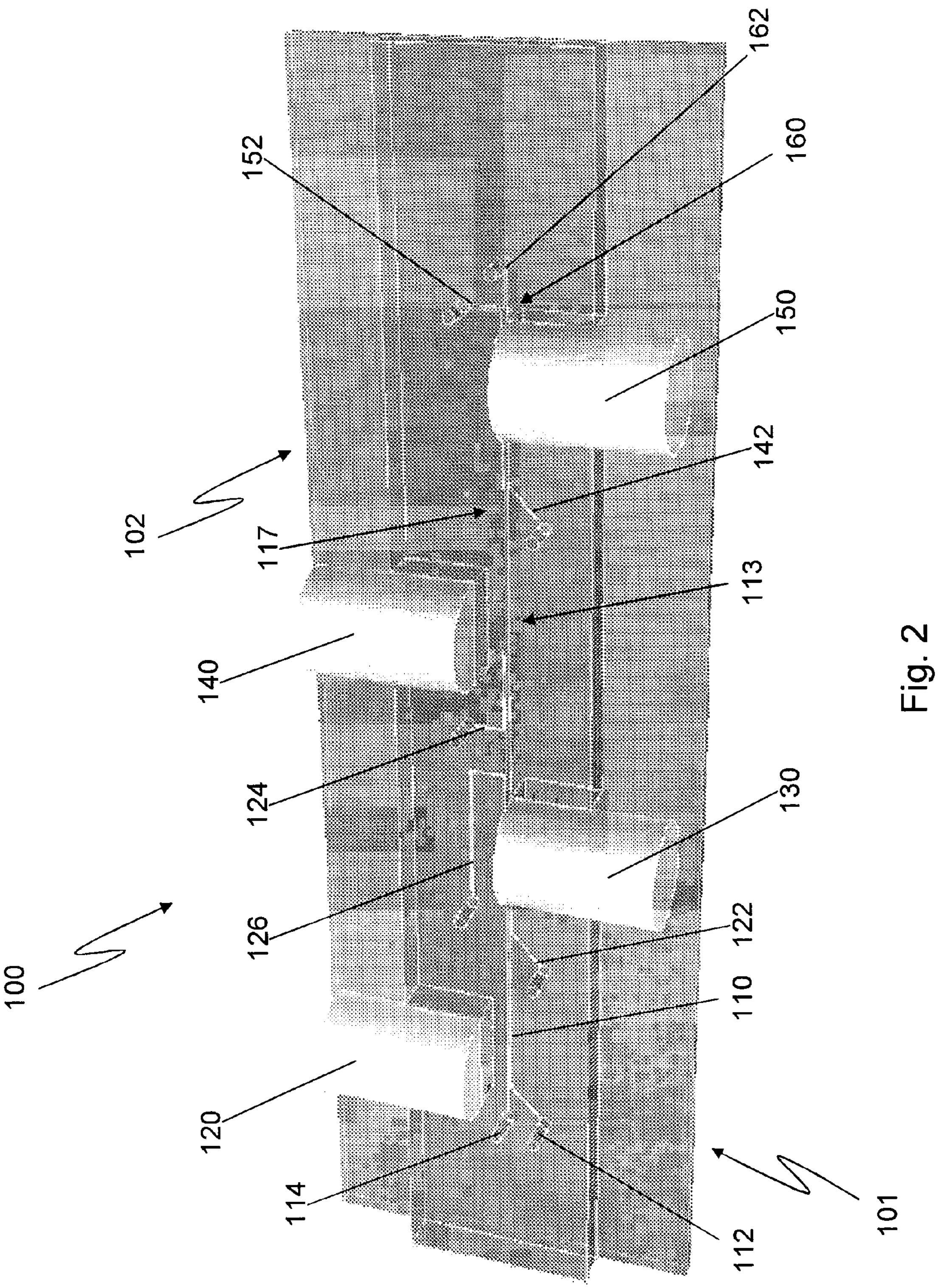
FIG. 2 illustrates a two-stage embodiment device.

By way of further example in which multiple stages are employed, reference is directed to the embodiment device 100 depicted in FIG. 2. The device 100 may be suited for use as an immunoassay developed for complement protein concentration measurement. The embodiment assay 100 may be suitable for target analyte concentrations in the micrograms per milliliter range with incubation times under one minute. The target analyte concentration range may be, by way of example, the human systemic range before and during cardiopulmonary bypass.

Generally, an immunoassay that utilizes beads involves a two-stage incubation with a preliminary step, in which the beads are initially processed to react with the target analyte, for example by coating the beads with a suitable primary antibody. By way of a specific example drawing upon the assays above, in the preliminary step the beads may be incubated with a biotinylated monoclonal anti-C3a (Assay Designs, Ann Arbor, Mich., catalog number GAU017-01B) at room temperature for 1 hour in an eppendorf tube. The beads are then ready to be used in the two-stage immunoassay.

Figure 8:
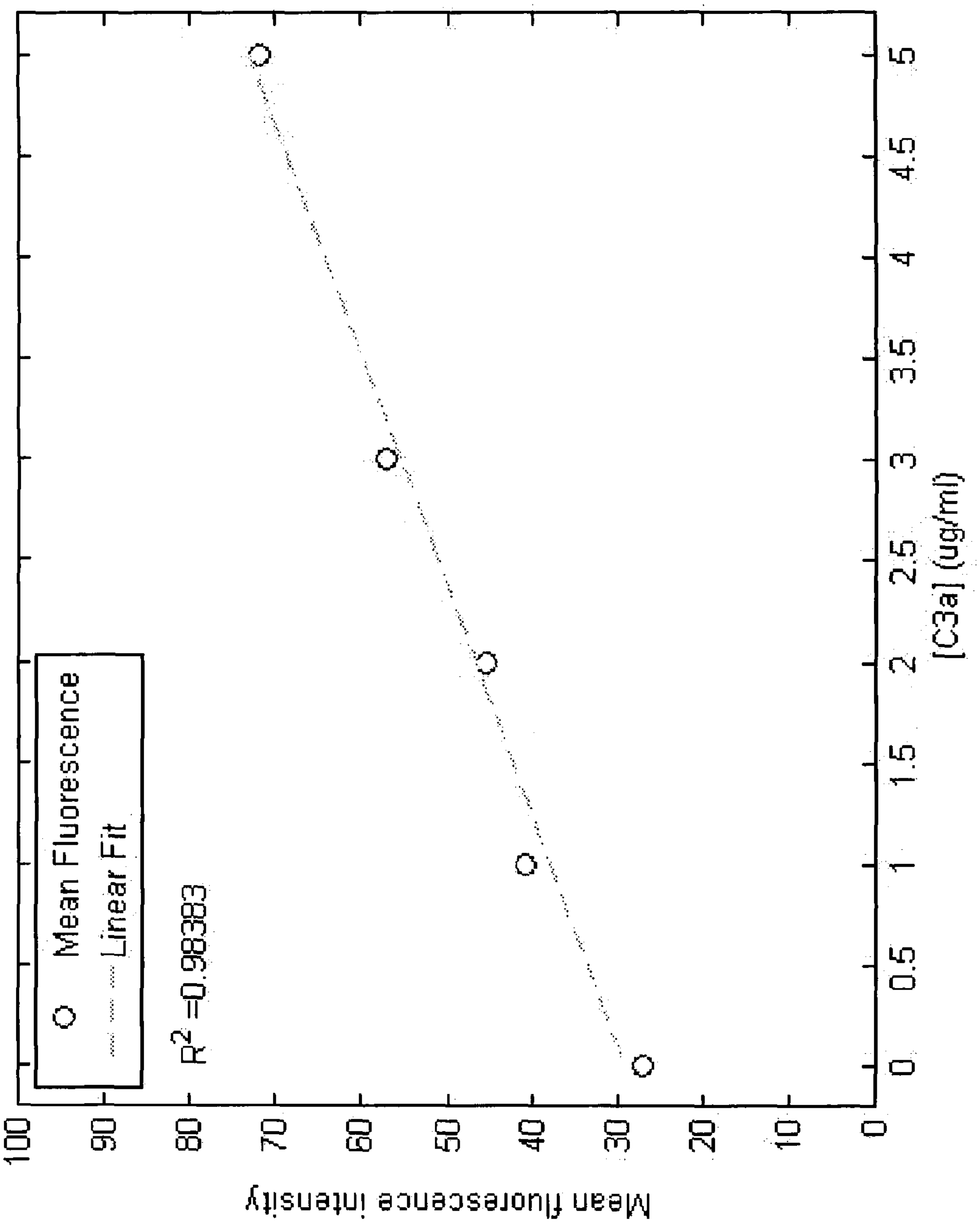
FIG. 8 is a graph showing mean fluorescence intensity from flow cytometer versus C3a concentration from bench-top testing of a two-stage immunoassay, with 45 second primary and secondary incubations.

In the first stage of the assay, the antibody-coated beads are incubated, again in an eppendorf tube, for 45 seconds with a C3a sample. The beads are then washed twice. Washing is accomplished by adding 1 ml of PBS, vortexing, centrifuging at 2,600×G for 1 minute, and aspirating the supernatant off the bead pellets. Next, the beads are incubated with a fluorescently tagged monoclonal secondary antibody (Assay Designs, catalog number GAU013-16) in excess concentration for 45 seconds. The secondary antibody binds a different epitope of the target analyte, in this example C3a, than the primary antibody. The amount of fluorescent antibody bound to the beads after the incubation is proportional to the target analyte antigen concentration in the sample, which enables measurement of antigen concentration based on fluorescence intensity. Fluorescent tagging of the secondary antibody is done with a phycoerythrin (PE) conjugation kit (Prozyme, Inc., San Leandro, Calif.). Results from bench-top testing for a C3a concentration range of 1 μg/ml to 5 μg/ml, including a negative control, are displayed in FIG. 8. The primary and secondary incubation times for these samples were 45 seconds.

Development of Microdevice Assay

The two-stage micro immunosensor 100 of FIG. 2 may be provided by combining the magnetic actuation technology from the single-stage device 1 with the two-stage bench top immunoassay described above. The magnetic actuation scheme used for this device 100 may be identical to that used for the single-stage device described above, except that it is run twice in a row; that is, the stages 101, 102 are serially connected to each other by way of the main fluidic channel 110 of the device 100, which may be dimensioned as discussed above with reference to the earlier embodiments. The micro immunoassay 100 may use, for example, the same beads as described above for both the two-stage bench top assay, as well as for the single-stage device which measured biotin-FITC concentration. The antibodies and fluorescent labeling kit used in the micro immunoassay 100 may be the same as those described above for typical two-stage bench top assays. Thus, the micro immunoassay 100 may provide the same functionality as a two-stage bench top assay except that it is completed entirely within the microdevice 100.

The two-stage micro immunosensor 100 may function in the same way as the single-stage embodiment 1. Paramagnetic beads are first processed so that they react with the target analyte in a manner that may be subsequently utilized for detection purposes, such as described above. The beads are then introduced into the main channel 110 via a bead inlet 112 of the main channel 110. The inlet channel 112 may be on a first side 113 of the main channel 110, and thus introduces the beads into the first side 113 of the main channel 110. The beads may be suspended in a carrier fluid having a density that is similar to the density of the beads, such as Ficoll-Paque PLUS. This balance in densities may help keep the beads from settling as quickly as they may otherwise do if using water as a carrier fluid. The bead inlet 112 preferably injects the beads into the main channel 110 at or upstream to the first magnet 120. For purposes of the following, "at" with respect to a magnet indicates positioning anywhere within the extents of the magnet along the channel 10. Washing/detection is performed by using second magnet 150 to position the beads into a detection region, while third magnet 130 and fourth magnet 140 are respectively used to position the beads for a first washing and for fluorescent tagging.

Figure 9:
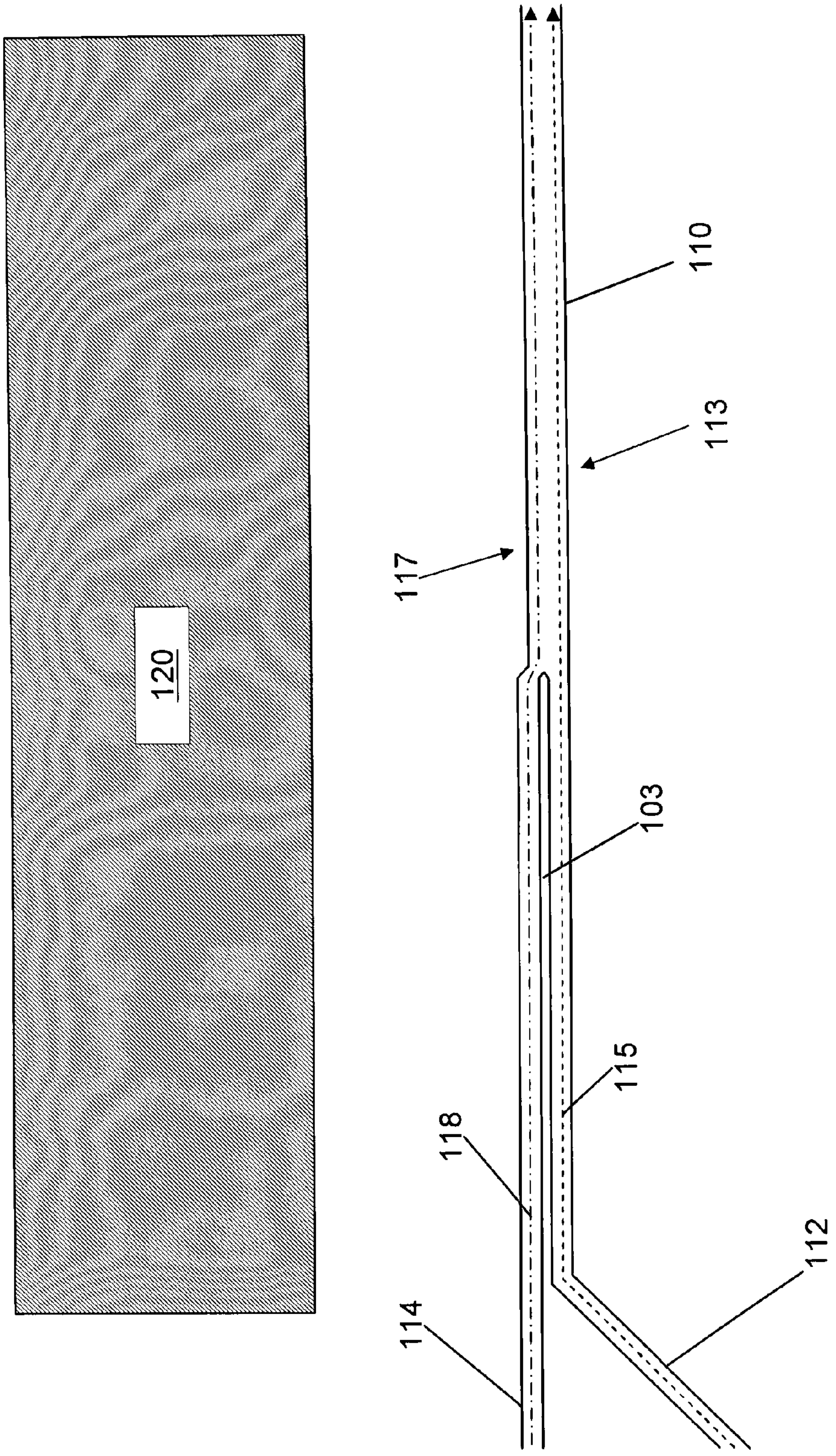
FIG. 9 is a detailed view of a sample inlet and a bead inlet for a main channel in an embodiment device.

A sample stream 118 containing the target analyte is introduced into the main channel 110 via sample inlet 114. The sample inlet 114 may be on a second side 117 of the main channel 110, and thus introduces the sample stream 118 into the second side 117 of the main channel 110. The sample inlet 114 preferably injects the sample stream 118 into the main channel 110 at or upstream to the first magnet 120. As shown in FIG. 9, in some embodiments as the beads approach the main channel 110, a special wall 103 may be provided to separate the beads from the sample stream 118 for a predetermined distance, such as the first 2.5 mm, where the magnetic field from the first magnet 120 is able to pull the beads to this wall 103 before the beads enter the sample stream 118. This may significantly increase the consistency of the incubation times of the beads within the sample stream 118. Without this wall 103, as was the design for the single-stage device 1 discussed above, the beads are free to enter the channel 110 at different positions along the cross-section of the channel 110, thus traveling different distances in the carrier fluid stream 115 before entering the sample stream 118.

Figure 10A:
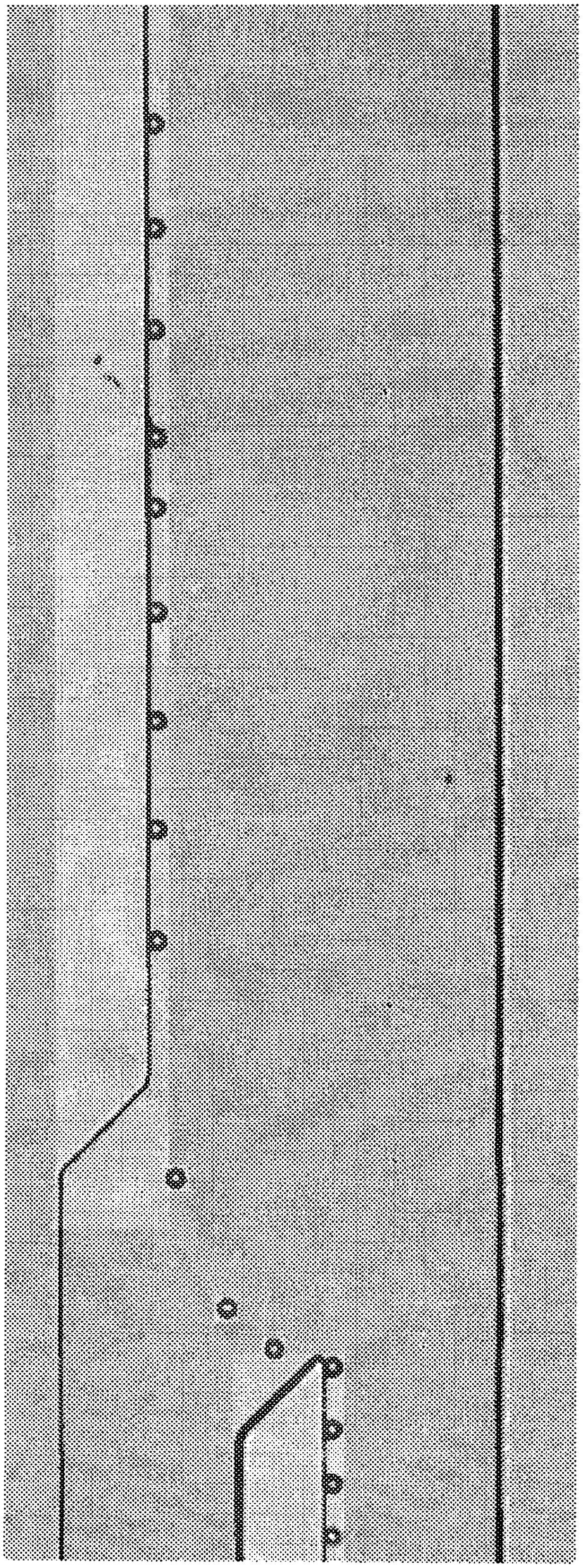
FIGS. 10A and 10B respectively show composite micrographs of beads being pulled into a sample stream and then being pulled away from a wall for transfer to a second stage.
Figure 10B:
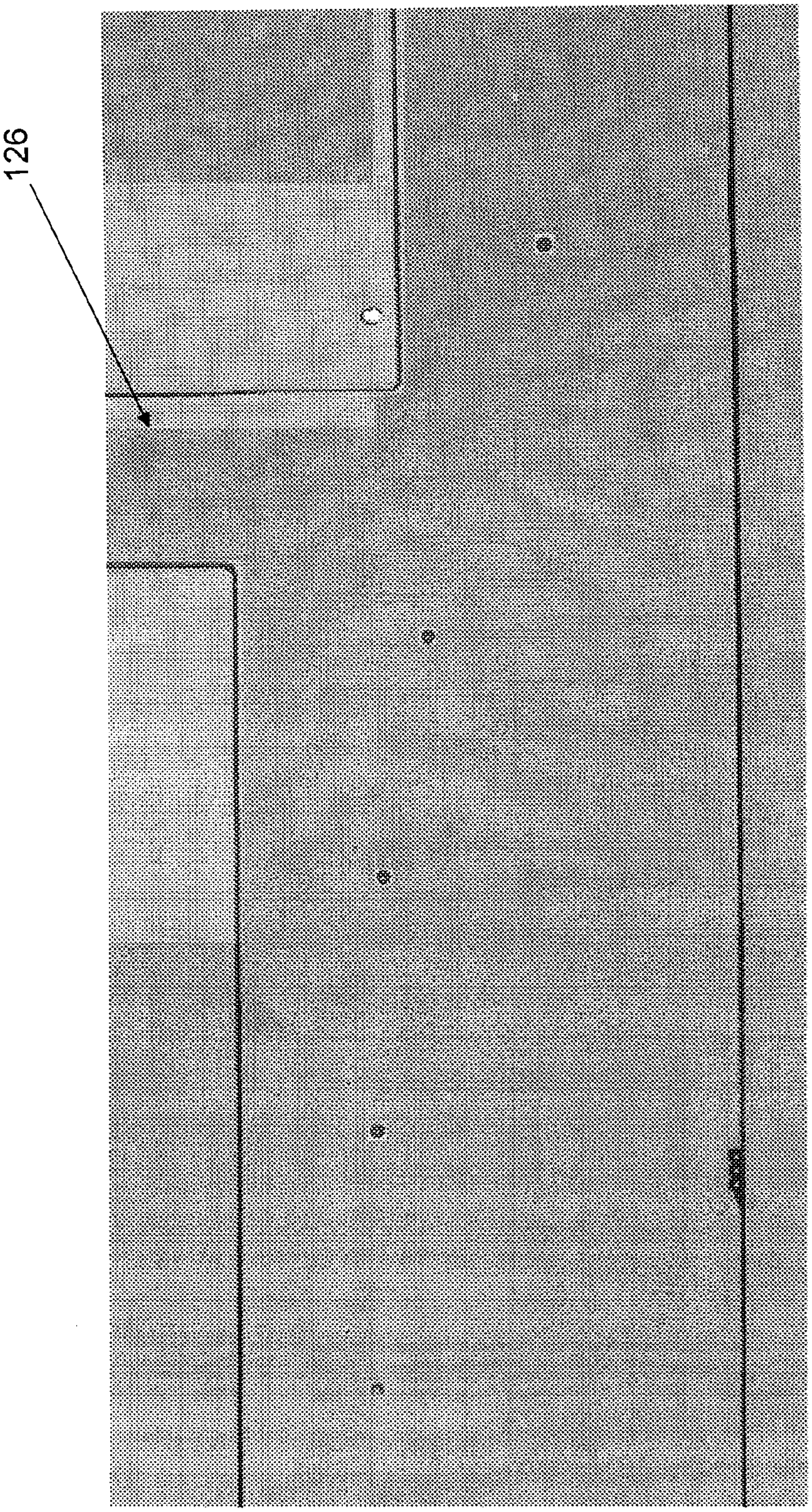

Upon entering the sample stream 118, the beads are pulled to the sidewall on the second side 117 of the channel 110 by the first magnet 120, and remain against the sidewall of the second side 117 of the channel 110 while being pulled down the length of the channel 110 by the fluid shear forces. As with the single-stage device 1, the beads move more slowly against the sidewall than they would farther from the sidewall. This phenomenon may increase the incubation time significantly compared to a design where the beads are not against the sidewall. The choice of magnets 120, 130, 140, 150 for this device (such as from K&J Magnetics, Jamison, Pa., catalog number B444), and the placement of the magnets 120, 130, 140, 150, is designed such that the beads are pulled to the respective sidewalls very quickly as they enter the channel 110, avoiding outlet channels, and remain against the sidewall until they are pulled away by the subsequent downstream magnet. At a predetermined location downstream, the force of the subsequent downstream magnet on the beads overcomes the force of the immediately prior upstream magnet, and the beads separate from the sidewall on one side 113, 117 of the channel 110 and are pulled toward the sidewall on the opposite side 117, 113 of the channel 110. FIGS. 10A and 10B respectively show composite micrographs of the beads being pulled into the sample stream 118, and then being pulled away from the sidewall for transfer to the second stage 102, avoiding an outlet channel 126.

In the second stage 102, the beads are pulled against the sidewall on the second side 117 of the main channel 110 by the fourth magnet 140 and thus into a tag stream of fluorescent secondary antibodies provided by a fluorescent secondary antibody tag inlet 124. This tag inlet 124 is configured to provide the tag stream of fluorescent secondary antibodies on the second side 117 of the main channel 110 at or upstream to the fourth magnet 140, and hence the fluorescent secondary antibody stream flows along the second side 117 of the main channel 110 past the fourth magnet 140. This antibody tag stream may be infused at a concentration that is sufficient to saturate all bound antigen on the beads. Thus, any variation in the amount of bound fluorescent secondary antibody is caused only by a difference in the amount of bound antigen.

Figure 11:
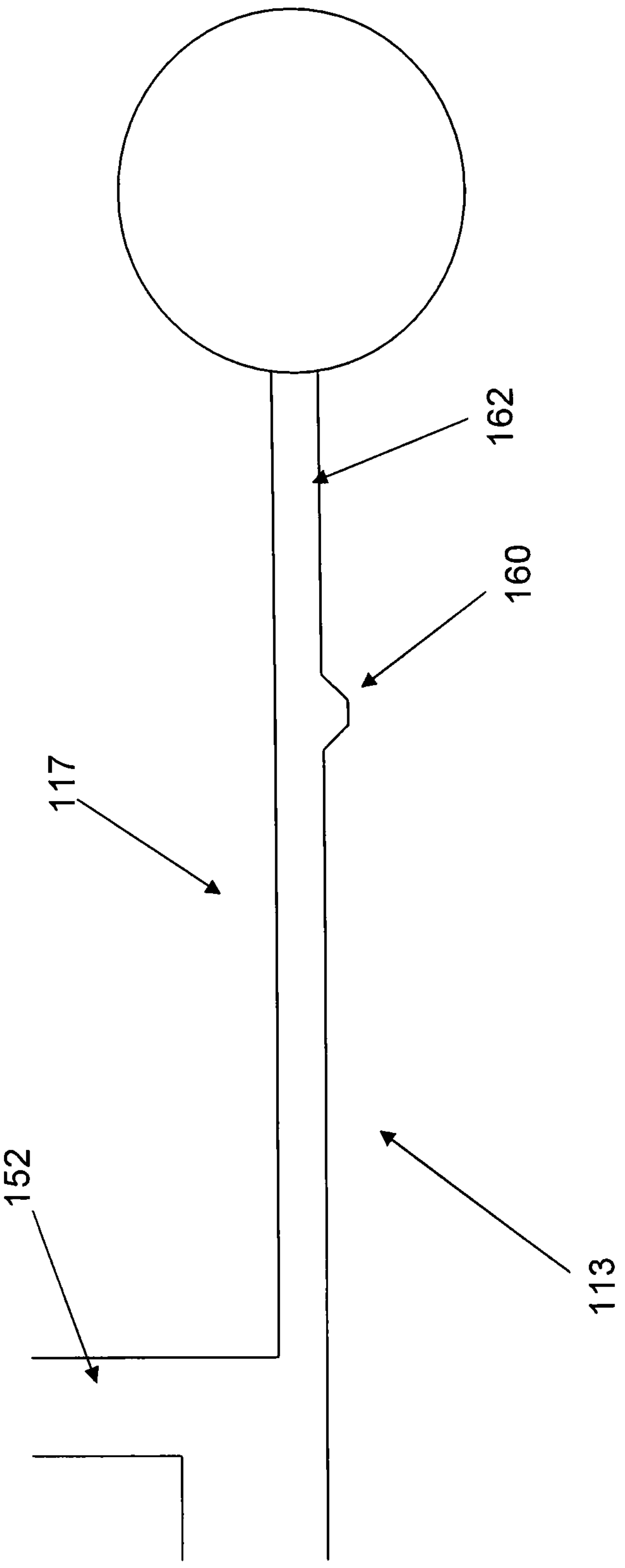
FIG. 11 shows a detection region in an embodiment device.

At the end of the main channel 110, the beads are pulled by the second magnet 150 toward the detection area 160 located on the first side 113 of the main channel 110, which is downstream from the second outlet 152. Once again the beads roll along the sidewall on the first side 113 of the main channel 110 in the device 100. FIG. 11 depicts a bead outlet channel 162 with the detection area provided by a divot 160 in the first side 113 sidewall. The bead outlet channel 162 is downstream from the detection region divot 160. The detection equipment, such as a laser beam, is focused in the detection divot 160. The purpose of this divot 160 is twofold. First, the divot 160 slows the bead velocity, since the widening of the channel 110 reduces the fluid velocity. As the bead velocity decreases, the PMT or equivalent detection equipment is able to capture more light or signal from the passing beads, thus making the detection more sensitive. The second purpose of the detection divot 160 is to reduce the background fluorescence or signal. Due to the length of the channel 110, a small amount of diffusional mixing occurs between the adjacent fluid streams. Therefore, the fluid in the bead outlet channel 162 includes a small amount of unbound fluorescent antibodies. These antibodies are present in a concentration gradient with the highest concentration on the second side 117, and the lowest concentration on the first side 113. By moving the detection equipment, such as the laser beam, farther from the fluorescent antibody side 117, the amount of unbound fluorescent antibodies flowing over the beam is significantly reduced, which lowers the background signal thus increasing the signal-to-noise ratio of the PMT or other detector output.

Figure 12A:
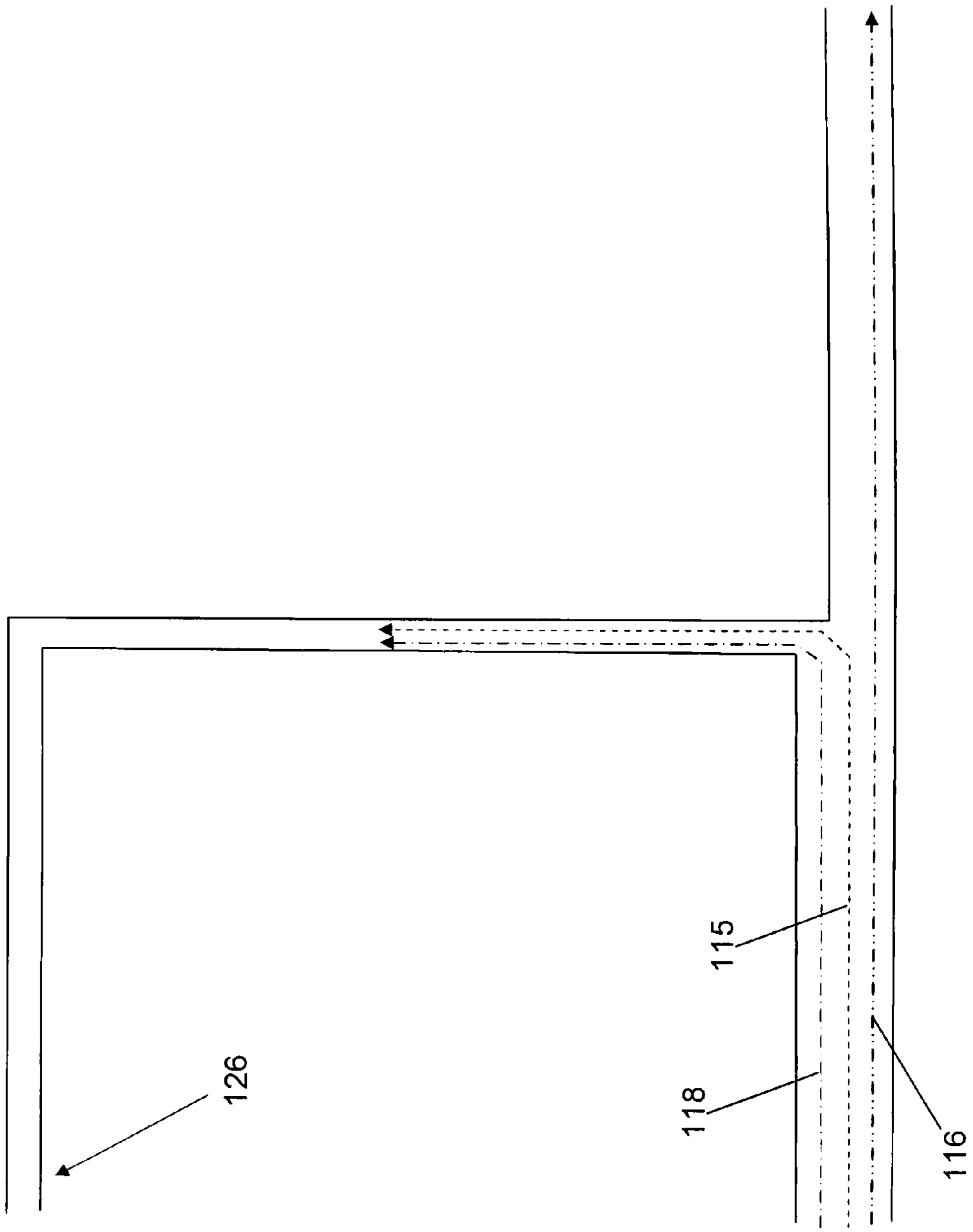
FIG. 12A shows a first transfer region for beads from a first stage to a second stage in a multistage device.

As with the single-stage device 1, the flow rate may be chosen to achieve the desired incubation time. The embodiment device 100 includes five inlets, all of which may use the same flow rate. These inlets include the bead inlet 112, the sample inlet 114, a first wash inlet 122, the fluorescent secondary antibody inlet 124, and a second wash inlet 142. The device 100 also includes three outlets 126, 152, 162, which run freely to waste without adding backpressure beyond the outlet ports. The outlet channels 126, 152, 162 may be designed to properly separate the flows based on internal backpressure. By way of example, there are two regions on the device 100 where flow separation may be desired. The first, shown in FIG. 12A, is the transfer region between the first stage 101 and the second stage 102. In this region, the sample stream 118 and the original bead carrier fluid 115 are directed to a first outlet 126, while a first wash stream 116 provided by first wash inlet 122 carries the beads to the second stage 102. The first wash inlet 122 is configured to deliver the first wash stream 116 on the first side 113 of the main channel 110 at or upstream to third magnet 130, while the first outlet channel 126 is disposed at or downstream from (i.e., is fluidly connected to the main channel 110 at or down stream from) the third magnet 130 and on the second side 117 of the main channel 110. Due to the flow resistance generated by the second stage 102, it may be desirable that the first outlet 126 is designed to be narrow and of considerable length to create sufficient backpressure to balance this resistance. A computational fluid dynamics software package (such as Comsol Multiphysics 3.3, Comsol Group) may be utilized to model the laminar flow in the device 100 and determine the desired length of the outlet channel 126.

Figure 12B:
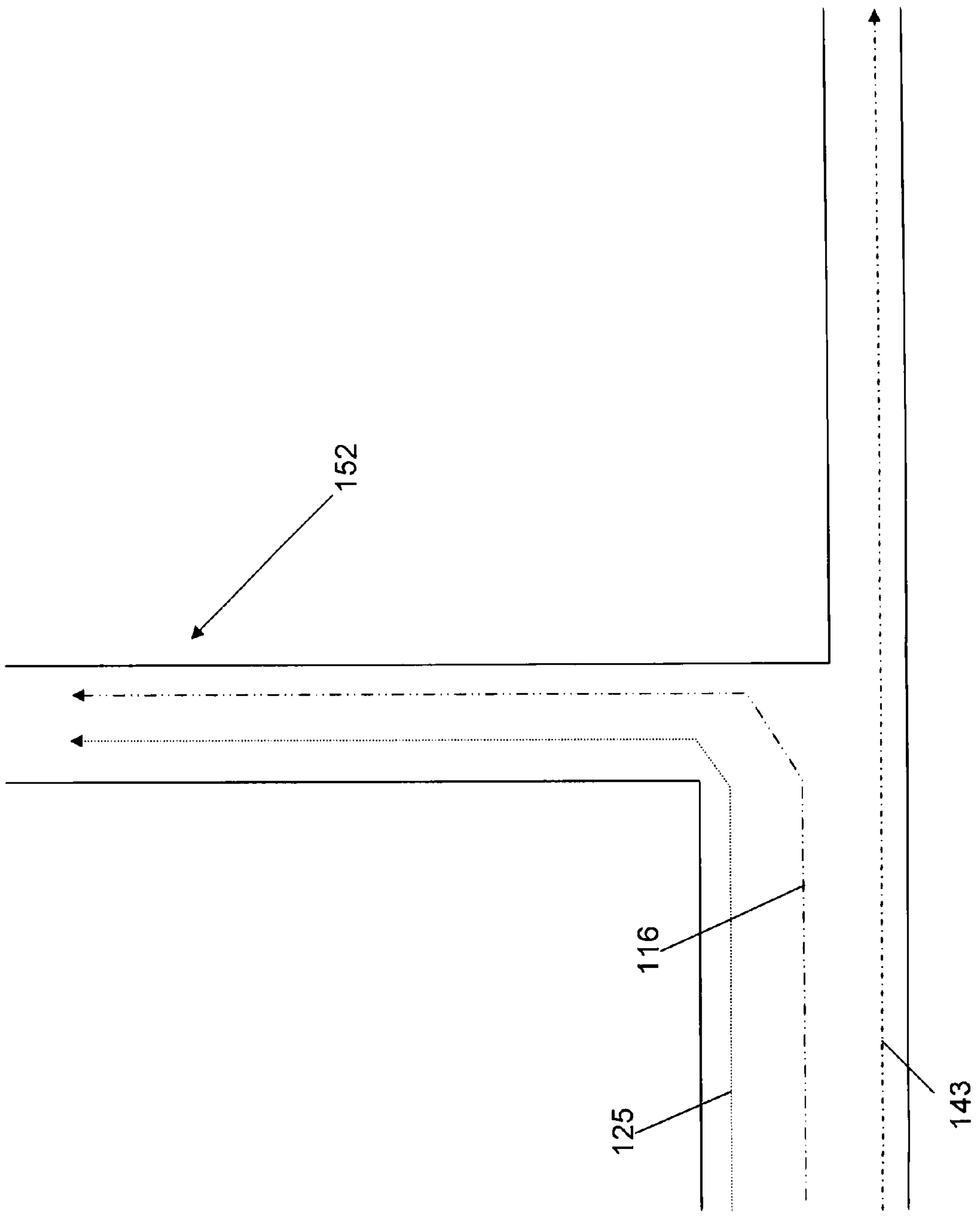
FIG. 12B shows a second transfer region in a multistage device for transferring beads to a detection pathway.

The second region where flow analysis may be required, shown in FIG. 12B, is where the fluorescent antibody stream 125 provided by inlet 124 and the bead transfer stream (i.e., the wash stream 116 from first stage 101) separate from the second wash stream 143 provided by second wash inlet 142. The second wash inlet 142 is configured to provide the second wash stream 143 at or upstream to the second magnet 150 and on the first side 113 of the channel 110 so that the second wash stream 143 flows along the first side 113 of the main channel 110 past the second magnet 150, while the second outlet channel 152 is disposed at (i.e., fluidly connected to the main channel 110 at) or downstream from the second magnet 150 and on the second side 117 of the main channel 110. The second wash stream 143 carries the beads to the detection area 160 depicted in FIG. 11, while the second outlet 152 removes the first wash stream 116 and the fluorescent antibody stream 125 from the main channel 110. The widths of the outlet channels 126, 152, 162 may thus be adjusted such that the streams are separated as described. Additionally, the relative positioning of the magnets 130, 150 and outlet channels 126, 152 may be adjusted to prevent accidental uptake of the beads into the outlet channels 126, 152. Preferably, the outlet channels 126, 152 are spaced relative to the magnets 130, 150 so that the outlets channels 126, 152 take up no more than 5% of the beads passing by the outlet 126, 152.

Figure 13:
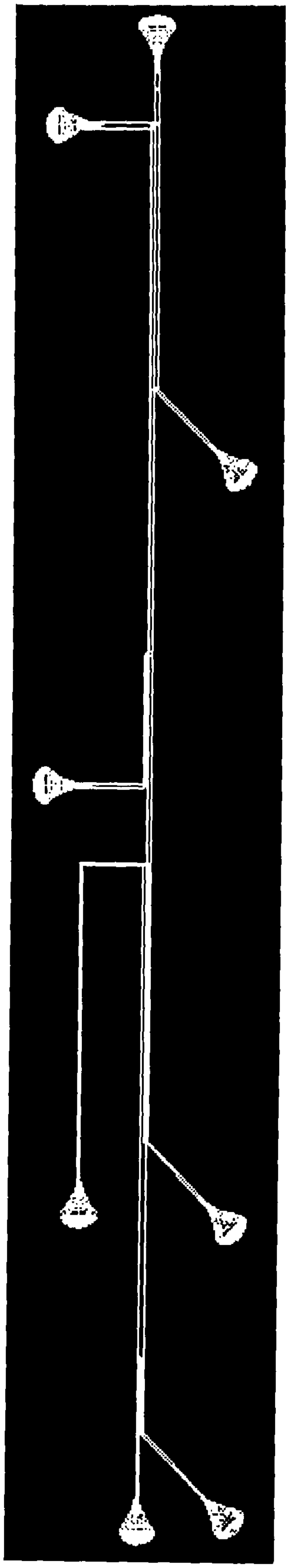
FIG. 13 shows a mask layout for an embodiment two-stage device.

A two-stage microdevice 100, like the single-stage embodiment 1, may be fabricated using standard soft lithography of PDMS. FIG. 13 shows an embodiment mask layout. This layout may be used to create a photomask for the photolithography of a master mold. The molds may be made with SU-8 2010 negative photoresist (Microchem, Newton, Mass.) or the like, on any suitable substrate, such as a 3 inch by 1 inch glass substrate. The photoresist may be spun, such as at 1000 RPM for 30 seconds, to achieve a desired depth, such as approximately 20 μm. The substrate may then be exposed to ultraviolet light at an appropriate exposure level, such as a total exposure energy of 150 $mJ/cm^2$. The substrate is then developed, for example for 3 minutes using SU-8 Developer. The final product may serve as a master mold, where the features are the inverse of the desired channels. Each PDMS chip can be made by pouring PDMS mixed with a crosslinking agent over the master to a suitable height, such as 4 mm, from the substrate surface. The PDMS is cured, such as at 65° C. for 1 hour. The cured PDMS is then peeled from the substrate, and the suitably sized chip is cut from the surrounding material. The inlet and outlet ports may be punched through with a needle or the like, such as a 19 gauge needle. The chip is may then be bonded to a suitably sized slide, such as a 3 inch by 1 inch glass slide. Bonding may be accomplished by treating the glass and PDMS mating surfaces with corona discharge and pressing the two together. The complete chip may then be placed in a 125° C. oven for 1 hour to ensure a strong bond. Subsequent to bonding, a template may be used to mark the magnet locations, and the magnet mounting notches may be cut, such as with a razor blade or the like.

Experiments with the microdevice 100 have been run on an epifluorescent microscopy platform. An adjustable device holder secured the chip above the 30× objective. The antibody coated beads, antigen sample, fluorescent secondary antibody solution, and the two wash fluids were loaded into 1 ml syringes. The syringes were placed on a syringe pump, and 0.1 inch ID Tygon tubing was run from each syringe needle to the appropriate inlet port. The tubing was pressed into the port using tweezers and was held tightly by friction. An argon ion laser beam was then focused on the detection area described above. The syringe pump was then turned on and run at a high rate to purge any air from the device. It was then set to the desired flow rate for the assay. After a brief settling time, data was recorded from the PMT output.

Figure 14:
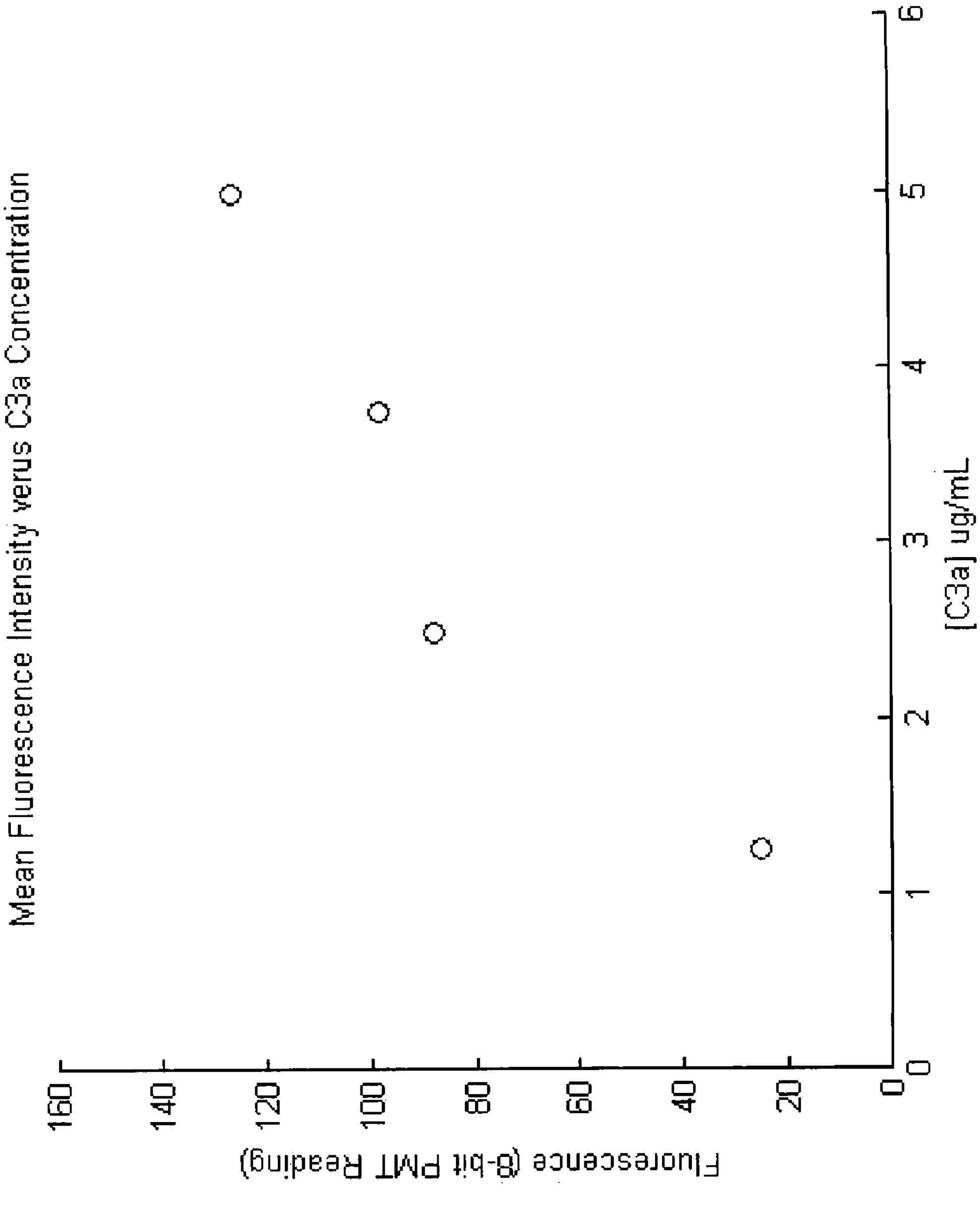
FIG. 14 is a graph of experimental data from an embodiment two-stage device.

The PMT output was sampled at 200 Hz. The output was recorded for a predetermined period of time, known as the sample period. As described for the single-stage device, the data from the PMT was processed by a 1 Hz high-pass filter and a peak finding algorithm. The following data were gathered from the system described above. Samples containing anaphylatoxin C3a in concentrations of 1.25 μg/ml, 2.5 μg/ml, 3.75 μg/ml and 5.0 μg/ml were run for 5 minute intervals, and the peak finding algorithm was used to find the fluorescence intensity maxima of beads passing the laser. The mean of the intensity maxima for each sample period is shown in FIG. 14. All flow rates were 0.1 μl/min, giving residence times around 45 seconds for each of the stages.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A microfluidic device for use in performing an assay for the presence of a target analyte in a sample fluid, the device comprising:

- a reservoir containing a fluidic carrier medium comprising magnetic beads, wherein the magnetic bead surfaces are configured to detectably interact with the target analyte; and
- a substrate on which there is disposed:
  - a main channel sized to accept said magnetic beads and permit the laminar flow of said fluidic carrier medium at a flow rate of at least 0.1 μl per minute along at least a portion of the main channel, the main channel having an upstream end, a downstream end, and opposing first and second sidewalls normal to said substrate;
  - a first inlet fluidly connected to the upstream end of the main channel and adapted to introduce a laminar flow of said fluidic carrier medium and magnetic beads into the main channel, wherein the first inlet is configured to introduce said fluidic carrier medium into the first sidewall of the main channel;
  - a second inlet fluidly connected to the upstream end of the main channel adapted to introduce a laminar flow of a sample stream comprising a target analyte into the second sidewall of the main channel;
  - a first magnet disposed adjacent to the second sidewall of the main channel and positioned to urge the magnetic beads passing the first magnet from the laminar flow of said carrier medium and into the laminar flow of said sample stream and towards the second sidewall;
  - a second magnet disposed downstream from the first magnet adjacent to the first sidewall of the main channel and positioned to urge the magnetic beads passing the second magnet towards the first sidewall, so that the magnetic beads exit the laminar flow of said sample stream before reaching the downstream end of said main channel; and
  - a detection region disposed downstream of said second magnet and configured to receive said magnetic beads after said beads exit the laminar flow of said sample fluid,
- wherein the main channel comprises a ridge projecting upwardly from said substrate at or upstream to the first magnet, the ridge separating the fluidic carrier medium from the sample stream, wherein the ridge begins upstream to the first magnet and terminates proximate to the first magnet.

2. The microfluidic device of claim 1 wherein the first inlet is configured to introduce the fluidic carrier medium and magnetic beads into a central region of the main channel between said first and second sidewalls.

3. The microfluidic device of claim 2 comprising a third inlet fluidly connected to the main channel and adapted to receive a laminar flow of a wash stream and to introduce said laminar flow of said wash stream into the first sidewall of the main channel.

4. The microfluidic device of claim 1 wherein the detection region comprises a divot in the first sidewall of the main channel.

5. A method for performing an assay for the presence of a target analyte in a sample fluid, the method comprising:

introducing a laminar flow of a fluidic carrier medium comprising magnetic beads, having surfaces that are configured to detectably interact with the target analyte, into a main channel disposed in a substrate and sized to accent said magnetic beads and permit a laminar flow of said carrier medium along at least a portion of the main channel, the main channel having an upstream end, a downstream end, and opposing first and second sidewalls upwardly disposed from said substrate, wherein the laminar flow of the fluidic carrier medium has a flow rate of at least 0.1 μl per minute and is introduced into the main channel through a first inlet fluidly connected to an upstream end of the main channel;

introducing a laminar flow of a sample stream comprising the tar analyte, wherein said laminar flow of said sample stream is introduced through a second inlet fluidly connected to the upstream end of the main channel along the second sidewall of the main channel;

magnetically inducing the magnetic beads to enter into the sample stream using a first magnet disposed adjacent to the second sidewall of the main channel and positioned to urge the magnetic beads passing the first magnet from the laminar flow of said carrier medium and into the laminar flow of said sample stream and towards the second sidewall;

magnetically inducing the magnetic beads to exit the sample stream using a second magnet disposed downstream from the first magnet adjacent to the first sidewall of the main channel and positioned to urge the magnetic beads passing the second magnet towards the first sidewall, so that the magnetic beads exit the laminar flow of said sample stream before reaching the downstream end of said main channel; and performing a detection step for the magnetic beads passing through a detection region disposed downstream of said second magnet and configured to receive said magnetic beads after said beads exit the laminar flow of said sample fluid.

6. The assay method of claim 5 wherein the detection step comprises an optical detection step.

7. The assay method of claim 5 wherein the magnetic beads are introduced into the first sidewall of the main channel.

8. The assay method of claim 5 wherein the magnetic beads exit the laminar flow of the sample stream into a wash stream.

9. The assay method of claim 8 wherein the magnetic beads are induced into a central portion of the fluidic channel.

10. The microfluidic device of claim 1, wherein length of said channel is selected to provide a residence time in said sample stream sufficient for detectable interactions between said magnetic bead surfaces and any target analyte in said sample stream.

* * * * *